US009375320B2

(12) United States Patent
Walker et al.

(10) Patent No.: US 9,375,320 B2
(45) Date of Patent: Jun. 28, 2016

(54) SPINAL IMPLANT DEVICES AND METHODS

(75) Inventors: John Lawrence Walker, Madison, MS (US); Michael Molleston, Hattiesburg, MS (US)

(73) Assignee: Spinal USA, Inc., Parsippany, NJ (US)

( * ) Notice: Subject to any disclaimer, the term of this patent is extended or adjusted under 35 U.S.C. 154(b) by 176 days.

(21) Appl. No.: 13/520,158

(22) PCT Filed: Dec. 28, 2010

(86) PCT No.: PCT/US2010/062243
§ 371 (c)(1),
(2), (4) Date: Feb. 25, 2013

(87) PCT Pub. No.: WO2011/082174
PCT Pub. Date: Jul. 7, 2011

(65) Prior Publication Data
US 2013/0144387 A1     Jun. 6, 2013

Related U.S. Application Data

(60) Provisional application No. 61/291,320, filed on Dec. 30, 2009.

(51) Int. Cl.
*A61F 2/44* (2006.01)
*A61F 2/46* (2006.01)
*A61F 2/30* (2006.01)

(52) U.S. Cl.
CPC .............. *A61F 2/442* (2013.01); *A61F 2/4611* (2013.01); *A61F 2002/30004* (2013.01);
(Continued)

(58) Field of Classification Search
CPC ................ A61F 2250/006; A61F 2002/30611; A61F 2002/30754; A61F 2002/4415; A61F 2002/448; A61F 2002/4485
USPC ........................................... 623/17.11–17.16
See application file for complete search history.

(56) References Cited

U.S. PATENT DOCUMENTS 5,836,148 A * 11/1998 Fukao ............................. 59/78.1
5,970,701 A * 10/1999 Roden et al. ..................... 59/78
(Continued)

FOREIGN PATENT DOCUMENTS

DE      19710392 C1 *  7/1999  ................ A61F 2/44
FR      2 913 331          9/2008
(Continued)

OTHER PUBLICATIONS

International Search Report and Written Opinion for PCT/US2010/062243, dated Dec. 28, 2010.
(Continued)

*Primary Examiner* — Anu Ramana
(74) *Attorney, Agent, or Firm* — Knobbe, Martens, Olson & Bear, LLP

(57) ABSTRACT

Systems, devices and methods relating to a spinal implant for placement in a disc space of a spine are described. A spinal implant (1) can include a plurality of wedge members including a leading wedge (22), a trailing wedge (28), and one or more intermediary wedges (26) therebetween. The spinal implant (1) can be configured to have a first linear configuration in which the plurality of wedge members are in a linearly expanded form and a second circular configuration in which the plurality of wedge members are positioned circumferentially relative to a center axis. In its first configuration, the spinal implant (1) can be delivered to a disc space, whereby it can assume its second configuration within the disc space, thereby forming a replacement nucleus. The spinal implant (1) can be kept in its first configuration by a rod member (41) received as through the plurality of wedge members. The wedge members can be slidably removed off of the rod member (41) and can assume the second configuration.

9 Claims, 9 Drawing Sheets

(52) U.S. Cl.
CPC ............... *A61F 2002/30156* (2013.01); *A61F 2002/30387* (2013.01); *A61F 2002/30579* (2013.01); *A61F 2002/30772* (2013.01); *A61F 2002/444* (2013.01); *A61F 2002/4415* (2013.01); *A61F 2002/4619* (2013.01); *A61F 2002/4631* (2013.01); *A61F 2220/0025* (2013.01); *A61F 2230/0023* (2013.01); *A61F 2250/0014* (2013.01)

(56) References Cited

U.S. PATENT DOCUMENTS

| | | | | |
|---|---|---|---|---|
| 6,136,031 | A * | 10/2000 | Middleton | 623/17.16 |
| 7,344,564 | B2 * | 3/2008 | Sweeney | 623/17.15 |
| 7,666,226 | B2 * | 2/2010 | Schaller | 623/17.11 |
| 7,947,078 | B2 * | 5/2011 | Siegal | 623/17.11 |
| 2006/0265077 | A1 | 11/2006 | Zwirkoski | |
| 2008/0133012 | A1 | 6/2008 | McGuckin | |
| 2008/0208255 | A1 * | 8/2008 | Siegal | 606/246 |
| 2008/0221687 | A1 | 9/2008 | Viker | |
| 2008/0312743 | A1 | 12/2008 | Vila et al. | |

FOREIGN PATENT DOCUMENTS

| | | |
|---|---|---|
| WO | WO 2008/036505 | 3/2008 |
| WO | WO 2008/084479 | 7/2008 |
| WO | WO 2008/152501 | 12/2008 |

OTHER PUBLICATIONS

Aug. 16, 2013 Search Report and Opinion for European Application No. 10841639.7 Filed on Jul. 26, 2012.

* cited by examiner

SPINAL IMPLANT DEVICES AND METHODS

REFERENCE TO RELATED APPLICATION

The present application is a United States national phase of PCT Patent Application No. PCT/US2010/062243, filed Dec. 28, 2010, entitled "Spinal Implant Devices and Methods," which claims priority under 35 U.S.C. §119(e) to U.S. Provisional Patent Application Ser. No. 61/291,320, entitled "Spinal Implant Devices and Methods," filed Dec. 30, 2009. The entire disclosure of each of the priority applications is hereby expressly incorporated by reference herein.

BACKGROUND OF THE INVENTION

1. Field of the Invention

The present application relates to devices and methods involving a spinal implant for placement in a disc space of a spine. For example, in some embodiments, the present application relates to devices and methods involving a nucleus replacement device for placement in a disc space of a spine. In some embodiments, the present application relates to devices and methods involving an intervertebral cage device for placement in a disc space of a spine.

2. Description of the Related Art

The spine relies on intervertebral spinal discs in between adjacent vertebrae to serve as mechanical cushions and transmit compressive loads. Spinal discs are composed of an outer annulus fibrosus that surrounds an inner nucleus pulposus. The annulus fibrosus is composed of laminae of fibrous tissue and fibrocartilage, while the nucleus pulposus is composed of water, chondrocytes, collagen fibrils and proteoglycan aggrecans that have hyaluronic long chains. The nucleus pulposus functions to distribute hydraulic pressure in all directions within each disc under compressive loads.

The nucleus pulposus, which begins early in life as eighty percent water, slowly desiccates with age. This causes the spinal disc to lose its cushioning ability and ability to bear loads, resulting in pain in the back and lower extremities. To resolve these problems, the degenerated nucleus may be removed and replaced. In some other cases, the nucleus may be removed and the vertebrae may be fused together in a spinal fusion procedure, which may include implanting an intervertebral cage and/or bone growth material to facilitate fusion of the vertebrae.

SUMMARY OF SOME EMBODIMENTS

There is a need to provide an improved spinal implant device that is easily implantable in an intervertebral disc space. According to one embodiment, a spinal implant device preferably comprises a plurality of wedge members coupled in series and configured to allow the wedge members to be delivered to a disc space. The wedge members preferably include surfaces for slidably coupling wedge members so that wedge members rotate circumferentially into position upon delivery to the disc space. The device preferably comprises an anchor to anchor the leading wedge to one or more vertebrae.

In some embodiments, devices and methods described herein can be used as an improved nucleus replacement device that can replace a degenerated nucleus. The nucleus replacement device preferably acts as a load bearing device, primarily in response to compressive forces, and restores or approximates natural spine biomechanics. In some other embodiments, devices and methods described herein can alternatively be used as intervertebral cage devices to facilitate fusion of intervertebral discs.

In some embodiments, a spinal implant system is provided for insertion in a disc space between a superior vertebra and inferior vertebra. The spinal implant system includes a plurality of wedge members comprising a leading wedge, a trailing wedge and one or more intermediary wedges positioned therebetween. The wedge members are coupled in series and configured to be delivered to the disc space. One or more of the wedge members includes a mating surface and a receiving surface for slidably coupling a mating surface of another wedge member. The mating surface of one or more wedge members can comprise a tongue, while the receiving surface of one or more wedge members can comprise a groove. The spinal implant system is configured to have a first configuration in which the plurality of wedge members are arranged for delivery to the disc space and a second configuration in which the plurality of wedge members are positioned circumferentially relative to a center axis. In the second configuration, the mating surface of the leading wedge is proximate to the receiving surface of the trailing wedge.

In some embodiments, a spinal implant system is provided for insertion in a disc space between a superior vertebra and inferior vertebra. The spinal implant system includes a plurality of wedge members comprising a leading wedge, a trailing wedge, and one or more intermediary wedges. The wedge members are coupled in series and are configured to be delivered to the disc space. The spinal implant system has a first configuration, in which the plurality of wedge members are arranged in a linearly expanded form for delivery to the disc space and a second configuration in which the plurality of wedge members are positioned circumferentially relative to a center axis.

In some embodiments, a spinal implant system is provided for insertion in a disc space between a superior vertebra and inferior vertebra. The spinal implant system includes a plurality of wedge members comprising a leading wedge, a trailing wedge and one or more intermediary wedges. The wedge members each include an aperture formed therein and are configured to be delivered to the disc space. The spinal implant system includes a first linear configuration in which the wedge members are in a linearly expanded form and a second circular configuration in which the plurality of wedge members are positioned circumferentially relative to a center axis. The spinal implant system further includes a rod member configured to hold the wedge members in the first linear configuration, wherein the rod member is receivable within the apertures of the plurality of wedge members such that the wedge members can be slidably delivered off of the rod member to assemble into the second circular configuration.

In some embodiments, a method of providing a nucleus replacement for an intervertebral disc space between a superior vertebra and an inferior vertebra of a patient is provided. The method comprises introducing a nucleus replacement device comprising a plurality of wedge members, including a leading wedge, a trailing wedge, and intermediate wedges; configuring the nucleus replacement device to be in a first configuration in which the plurality of wedge members are placed in a linear expanded form; delivering the nucleus replacement device through a hole in the patient; introducing the nucleus replacement device into the intervertebral disc space, wherein the leading wedge is introduced first into the intervertebral space; and configuring the nucleus replacement device to be in a second configuration in which the plurality of wedge members are placed circumferentially to a central axis within the intervertebral disc space.

DETAILED DESCRIPTION OF EMBODIMENTS

Some embodiments of the present application are directed to a spinal implant device for placement in a disc space of a spine. A spinal implant device preferably is capable of being implanted in a disc space with ease. According to one embodiment, a spinal implant device for insertion in a disc space between a superior vertebrae and an inferior vertebrae comprises a plurality of wedge members comprising a leading wedge, a trailing wedge, and one or more intermediary wedges positioned therebetween. The wedge members are coupled in series and comprise apertures configured to allow the wedge members to be slidably delivered over a rod member during insertion. One or more of the wedge members includes a mating surface and a receiving surface for slidably coupling a mating surface of another wedge member. The mating surface of the one or more of the wedge members comprises a tongue and the receiving surface of the one or more of the wedge members comprises a groove. An anchor can be positioned at a tip of the leading wedge such that it is positionable relative to one or more of the superior vertebrae and inferior vertebrae. In some embodiments, the spinal implant device can have a first configuration in which the plurality of wedge members are substantially linearly aligned for insertion and a second configuration in which the plurality of wedge members are positioned circumferentially relative to a center axis along the anchor position. In some embodiments, the spinal implant device can have a first configuration in which the plurality of wedge members are arranged in a curved configuration for insertion. In the second configuration the mating surface of the leading wedge is proximate to the receiving surface of the trailing wedge.

Some embodiments of the present application are directed to a nucleus replacement device for placement in a disc space of a spine. A nucleus replacement device preferably mimics the natural functionality of a nucleus and is capable of being implanted in a disc space with ease. In some other embodiments, devices and methods described herein can alternatively be used as intervertebral cage devices to facilitate fusion of intervertebral discs. While the embodiments described herein will generally reference the spinal implant as a nucleus replacement device, one of ordinary skill in the art will understand that similar structures, features and advantages of the present embodiments are applicable to intervertebral cage devices and other spinal implants. Thus, references to specific procedures or implants are exemplary and not exclusive.

Figure 1A:
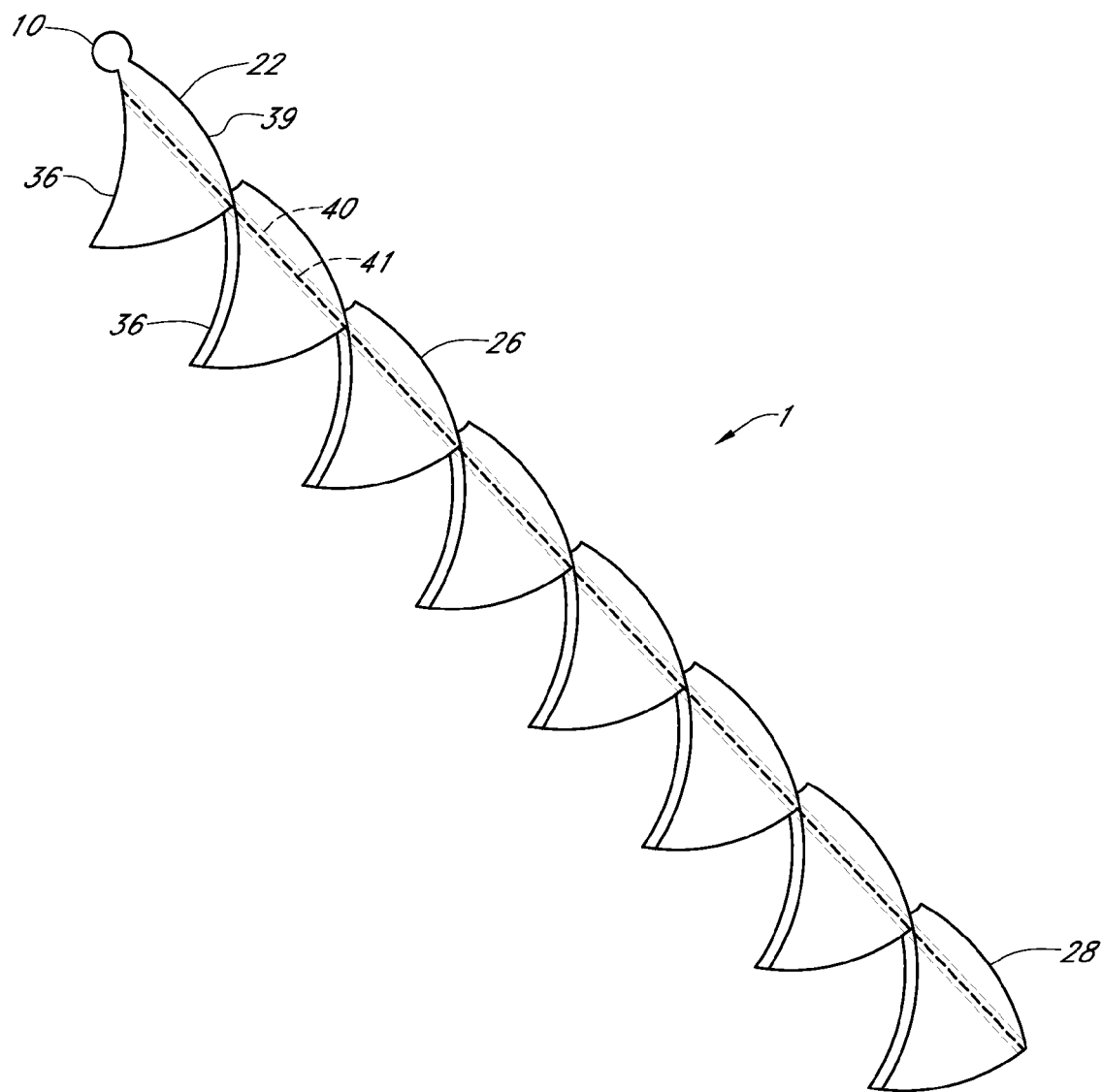
FIGS. 1A-1C illustrate a spinal implant device according to one embodiment of the present application.
Figure 1B:
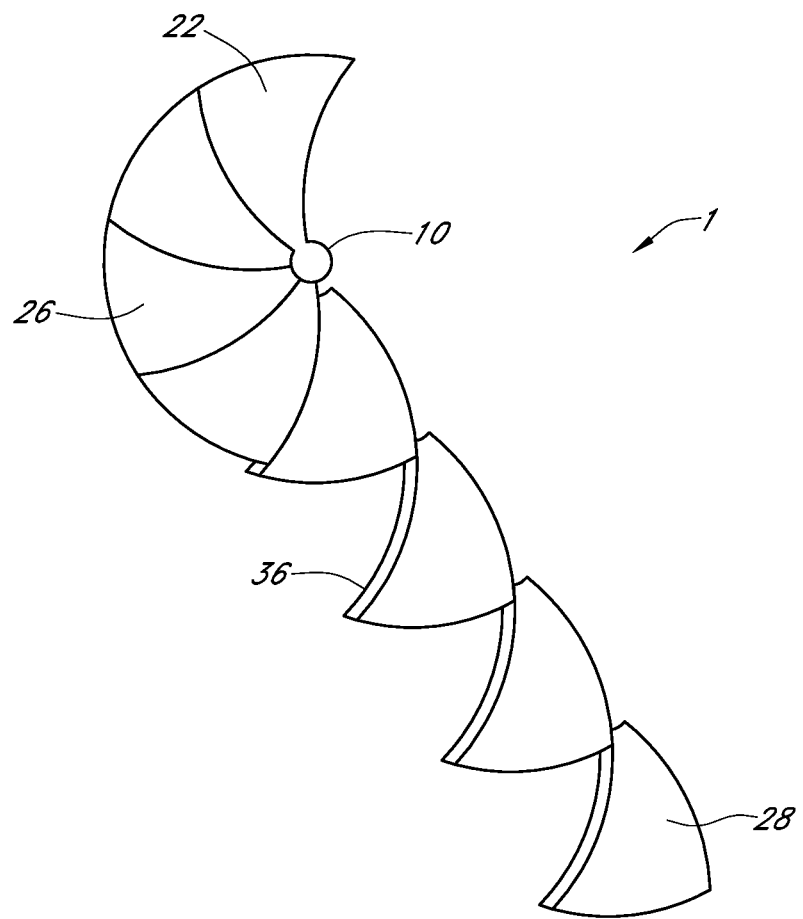
Figure 1C:
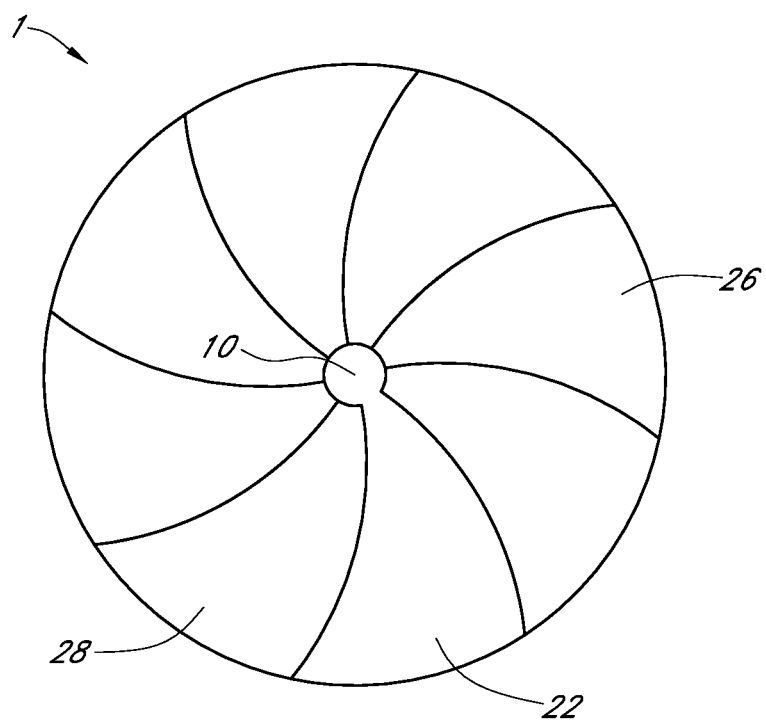

FIGS. 1A-1C illustrate a nucleus replacement device according to some embodiments of the present application. FIG. 1A illustrates a nucleus replacement device in an initial configuration. FIG. 1B illustrates the nucleus replacement device of FIG. 1A in an intermediary configuration. FIG. 1C illustrates the nucleus replacement device of FIG. 1A in a final configuration.

FIG. 1A illustrates a nucleus replacement device 1 in an initial configuration in a linearly expanded form. The nucleus replacement device 1 includes a plurality of wedge members including a leading wedge 22, a trailing wedge 28 and one or more intermediary wedges 26 located therebetween. Each of the wedge members preferably includes a mating surface 36 and a receiving surface 39, and a hole or aperture 40 through which a rod member 41 can be inserted. The leading wedge 22 also preferably includes a peg or anchor 10 at its tip.

As shown in FIG. 1A, the plurality of wedge members have an initial configuration in which the wedge members are placed linearly. In some embodiments, in the initial configuration, the wedge members can be positioned in a curved arrangement. The wedge members are preferably connected to one or more other wedge members in series, as discussed further below. The plurality of wedge members are capable of coming together to form a circular nucleus replacement device 1 (shown in FIG. 1C) having a center axis that mimics the form and/or natural function of a natural nucleus.

In the embodiment in FIG. 1A, each of the wedge members is generally triangularly-shaped and includes an apex or tip. In addition, each of the wedge members is sized similarly. One skilled in the art will appreciate that other shapes and sizes may be used. In addition, while the wedge members can be primarily solid (e.g., with the exception of an aperture in some embodiments), one or more wedge members can also have a largely hollow section. Having a largely hollow section advantageously allows for bone ingrowth in the wedge members, which is beneficial if the wedge members function as part of an intervertebral cage.

Each of the wedge members preferably includes a mating surface 36 and a receiving surface 39 for slidably coupling a mating surface 36 of another wedge member. In some embodiments, the mating surface 36 comprises a protrusion, extension, flange or tongue (e.g., a dovetail tongue), while the receiving surface 39 comprises a complementary notch, slot, track or groove. By sliding the mating surface 36 (e.g., tongue) of one wedge member into the receiving surface 39 (e.g., groove) of another wedge member, the wedge members can be securely coupled. While each of the wedge members preferably includes a mating surface 36 and a receiving surface 39, in some embodiments, individual wedge members can have mating and receiving surfaces that differ from mating and receiving surfaces of other wedge members. For example, the mating and receiving surfaces of an intermediary wedge 26 that is coupled to two other intermediary wedges 26 can differ from the mating and receiving surfaces of a trailing wedge 28 that is configured to be coupled to a leading wedge 22 and an intermediary wedge 26.

The mating surface 36 of a first wedge member can slidably couple with the receiving surface 39 of a second wedge member such that the two wedges are secured together. As shown in FIG. 1A, in the initial configuration, the wedge members are already securely coupled; a portion of the mating surface 36 of a first wedge member is coupled to a portion of the receiving surface 39 of a second wedge member. The mating surface 36 of the first wedge member can be slidably received in the receiving surface 39 of the second wedge member such that the two surfaces are completely mated and unexposed. For example, as shown in FIG. 1B, the receiving surface (not shown) of the leading wedge 22 is mated with the mating surface (not shown) of an adjacent intermediary wedge 26 such that the two surfaces are unexposed.

The material of the wedge members can include various types of material that allow the nucleus replacement device 1 to suitably replicate or mimic the natural function of a nucleus. Among the materials that can be used for the wedge members include various polymeric materials, such as elastomeric materials, hydrogels or other hydrophilic polymers and composites. Specific elastomeric materials can include silicone, polyurethane, co-polymers of silicone and polyurethane, polyolefins, neoprene, nitrile, vulcanized rubber and combinations thereof. In some embodiments, the wedge members are composed of PEEK (filled or unfilled), titanium, stainless steel, tantalum, chrome cobalt alloys, or combinations thereof. Preferably, in some embodiments, the chosen materials will be biocompatible and capable of absorbing and distributing compressive loads.

In some embodiments, the material of the individual wedges is homogeneous. In other embodiments, individual wedges can be formed of two or more materials. For example, in some embodiments, a wedge member can have an outer shell formed of a first material and an inner core formed of a second material. In addition, in some embodiments, the material composition of one wedge member can be different from the material composition of other wedge members, such that the nucleus replacement device can have properties that vary with each individual wedge member. In some embodiments, the wedge members can include a variety of surface configurations, including macro-surface patterns. Other physical modifications can include a microtexturized surface formed by bead-blasting, plasma etching or chemical etching. In some embodiments, physical modification results in a roughened surface that increases the friction of the wedge surfaces and the ability of the surfaces to mate with complementary surfaces.

Each of the wedge members is sized to be inserted into a small space or opening, preferably one at a time. In some embodiments, the wedge members can be appropriately sized such that the wedge members can be placed one at a time through an opening formed in an annulus fibrosus.

Internally, through each of the wedge members, is an opening or aperture 40, formed, for example, by drilling or molding. A rod member 41 can be positioned within the apertures. The rod member 41, in some embodiments, is preferably cylindrical in shape with a generally circular cross-section, although the rod member need not be limited to this particular shape. In some embodiments, the rod member 40 is composed of a plastic (e.g., polyurethane) or a metal (e.g., stainless steel).

As shown in the initial configuration in FIG. 1A, the rod member 41 serves to hold the wedge members in a linear formation. During implantation of the device, individual wedge members can be slidably delivered from the rod member 41 in series, beginning with the leading wedge 22. In some embodiments, a push rod (not shown) is provided that can be used to push or slide the wedge members off of the rod member 41 by applying a pushing force (e.g., to the trailing wedge 28). The push rod can be used to push off the wedge members from the rod member 41 one at a time. Once delivered from the rod member 41, the wedge members are designed to assemble into a configuration different from that of the initial configuration, as shown in FIGS. 1B and 1C. For example, wedge members that are in a first linear configuration can be delivered from a rod member and assembled into a second circular configuration.

In other embodiments, the wedge members can be delivered into a disc space without using a rod member 41. For example, the wedge members can be delivered through a port or sleeve member (not shown) with or without using the rod member 41. The sleeve member can serve as a guide that directs the wedge members to an appropriate location in a disc space. Alternatively, the wedge members can also be delivered over a member less rigid than a rod member, such as a suture. In other embodiments, the wedge members can be delivered "freehand" (e.g., without the assistance of a rod, sleeve member, or suture to guide delivery of the implant).

While the embodiment in FIG. 1A illustrates eight wedges slidably delivered over the rod member 41, in other embodiments, the number of wedges will differ. In some embodiments, the number of wedges will be between two and fifteen, and in some embodiments, greater than fifteen. One skilled in the art will appreciate that the number of wedges can be any number, so long as the wedges are capable of compacting to form a nucleus replacement of a suitable shape and form.

As shown in FIG. 1A, leading wedge 22 also preferably includes a peg or anchor 10 at its tip. The anchor 10 is capable of being inserted into one or more vertebrae and can be used to hold the nucleus replacement device 1 in a position relative to one or more adjacent vertebrae. In some embodiments, the anchor 10 is formed as part of the leading wedge 22 (e.g., as a monolithic piece formed by a single mold), while in other embodiments, the anchor 10 is formed separately and attached to the leading wedge 22. In some embodiments, the anchor 10 can be between between 1 mm and 5 mm long. In some other embodiments, the length of the anchor can approach 0 mm or be greater than 5 mm. In some embodiments, the anchor 10 serves as a center axis for the nucleus replacement device 1 in its final configuration, as shown in FIG. 1C. In some embodiments, the leading wedge does not comprise an anchor or peg. One skilled in the art will appreciate that the leading wedge 22 need not include a peg or an anchor (e.g., the leading wedge 22 can therefore have a shape similar to other wedge members, including the intermediary wedges and trailing wedge).

FIG. 1B illustrates the nucleus replacement device 1 of FIG. 1A in an intermediary configuration. While some of the wedge members remain in a linear formation in the intermediary configuration, such as trailing wedge 28, other wedge members that have been delivered from the rod member 41 (e.g., by using a pushing rod) begin to resemble a portion of a circular nucleus. Upon being delivered or pushed off of the rod member 41, the wedge members are designed such that the mating surface 36 of one wedge member is slidably coupled to the receiving surface 39 of another wedge member. The wedge members delivered from the rod member 41 are positioned circumferentially relative to the anchor 10, which has been fixed in position relative to one or more vertebrae and serves as a center axis for the nuclear replacement device in its final configuration, as shown in FIG. 1C.

FIG. 1C illustrates the nucleus replacement device 1 of FIG. 1C in a final configuration in which it resembles a circular nucleus having the anchor 10 as a center axis. Each of the wedge members is preferably slidably coupled to an adjacent wedge member such that the mating surfaces and receiving surfaces of the wedge members are not exposed. In some embodiments, the circular nucleus replacement device 1 has a radius of between 10 mm and 50 mm. In other embodiments, the nucleus replacement device 1 does not resemble a circular nucleus in its final configuration, but rather is elliptical, rectangular, or any other suitable shape. In addition, in some embodiments, the nucleus replacement device 1 in its final configuration is not symmetrical, but rather is asymmetrical.

Figure 2A:
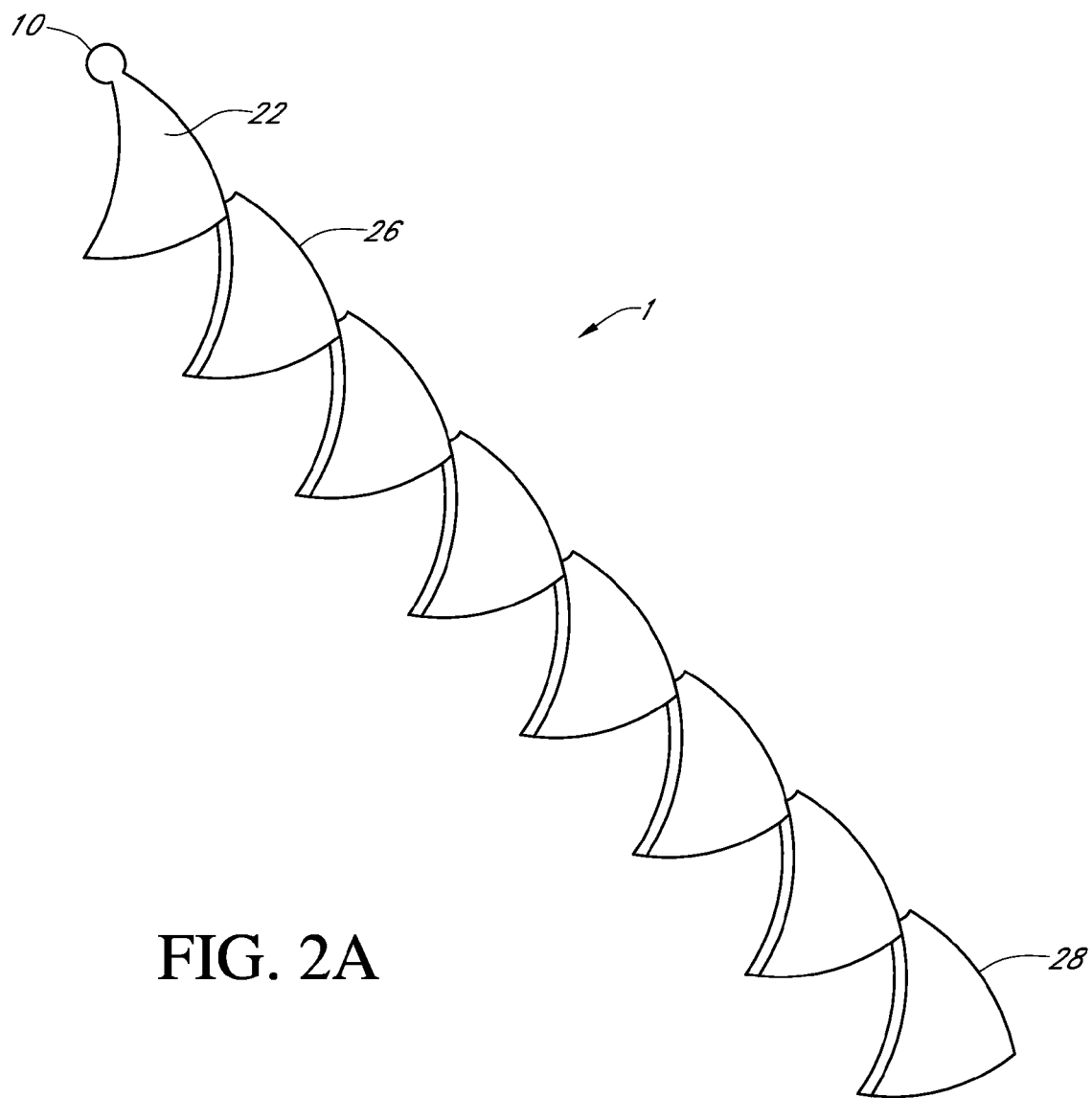
FIGS. 2A-2C illustrate different views of a spinal implant device according to an alternative embodiment of the present application.
Figure 2B:
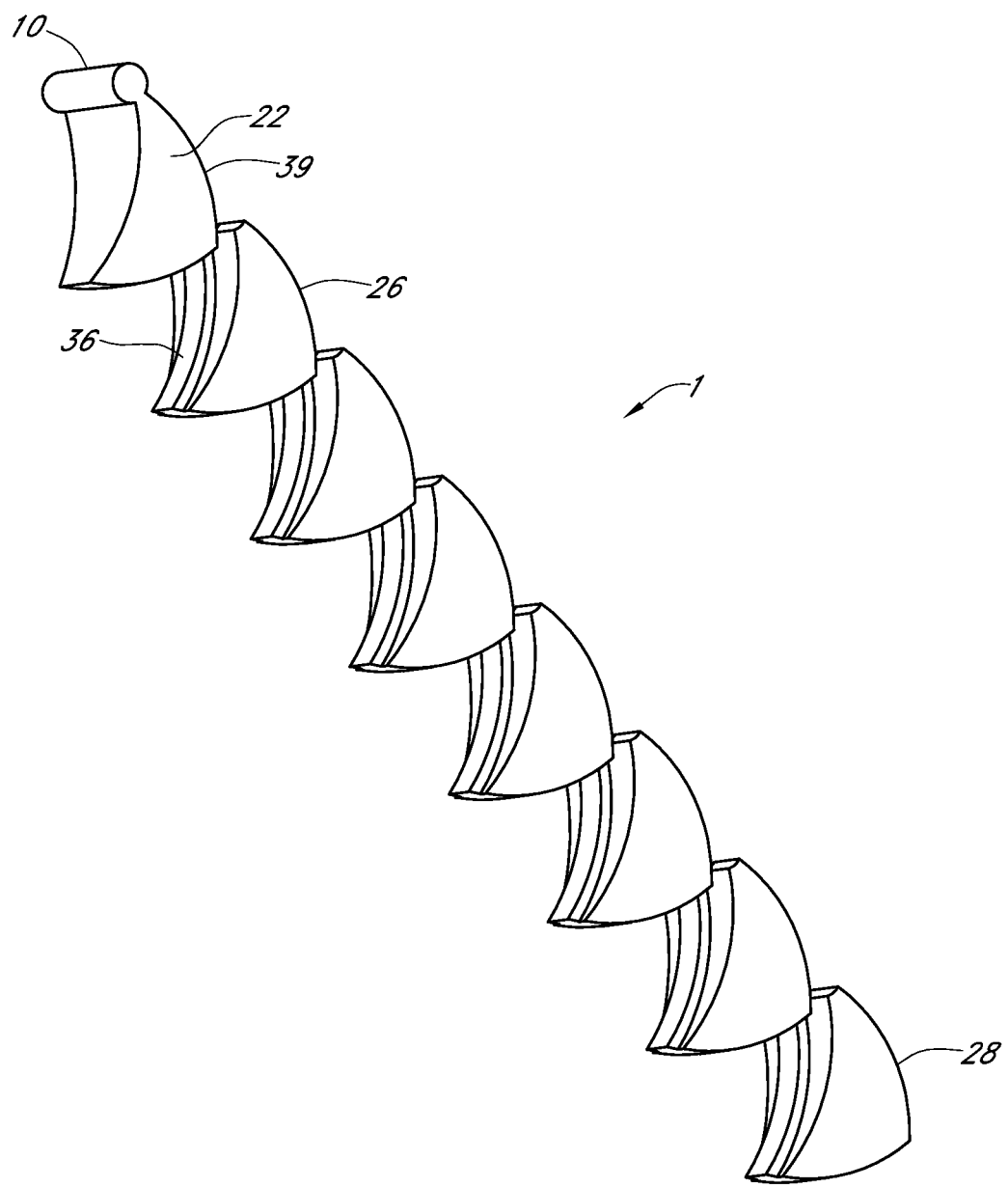
Figure 2C:
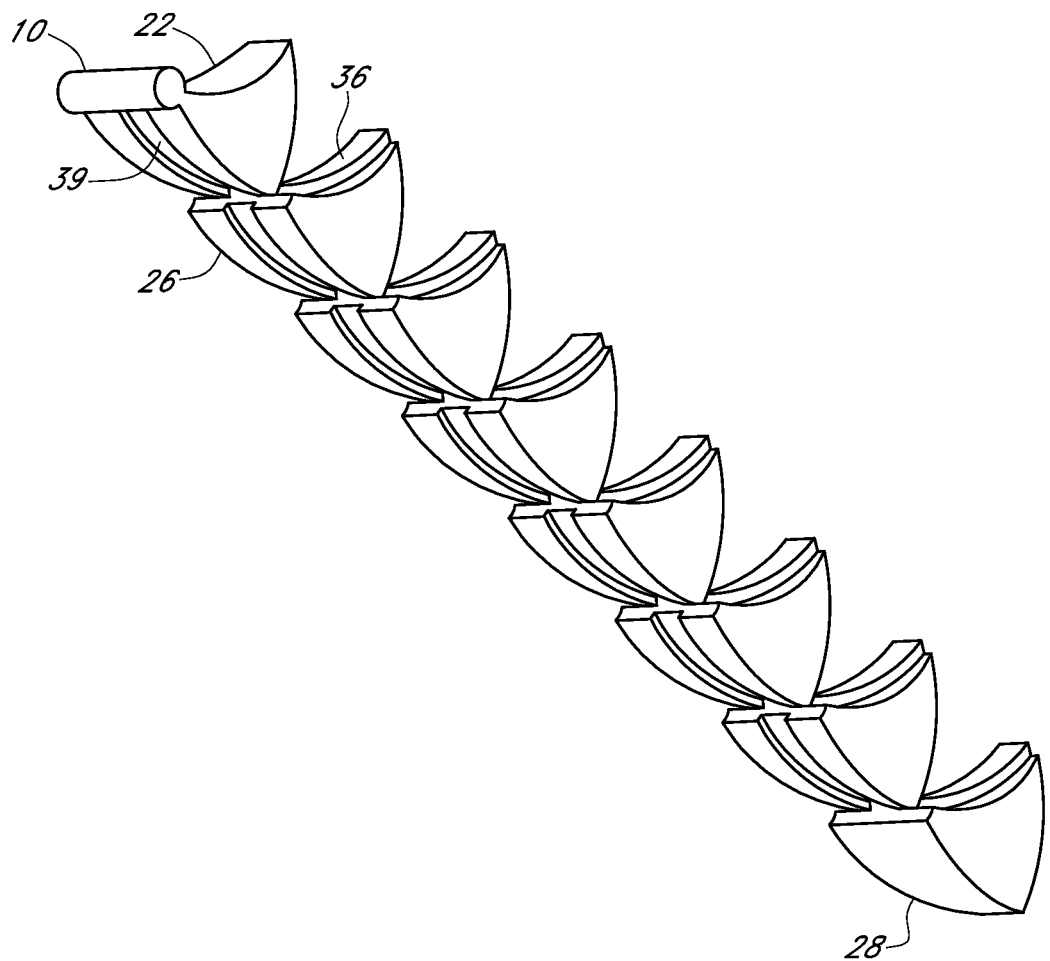

FIGS. 2A-2C illustrate different views of a nucleus replacement device in an initial configuration according to alternative embodiments of the present application. In each of FIGS. 2A-2C, the nucleus replacement device 1 is in an initial configuration in which the device is in a linearly expanded form. Specific features, such as the mating surfaces 36 and receiving surfaces 39 of one embodiment, are prominently shown in these figures.

FIG. 2A illustrates a side view of the nucleus replacement device 1 in an initial configuration. The nucleus replacement device 1 includes a leading wedge 22 affixed to an anchor 10, intermediary wedges 26 and trailing wedge 28. From this viewpoint, the anchor 10 of the leading wedge 22 is clearly shown and resembles a cylindrical piece that is formed with the leading wedge 22.

FIG. 2B illustrates a front perspective view of the nucleus replacement device 1 of FIG. 2A in an initial configuration. From this viewpoint, the mating surfaces 36 of the wedge members are clearly shown. The mating surfaces 36 resemble tongues or extensions that protrude beyond the surfaces of the wedge members. The mating surfaces 36 can be slidably mated with receiving surfaces 39, shown prominently in FIG. 2C.

FIG. 2C illustrates a rear perspective view of the nucleus replacement device 1 of FIG. 2A in an initial configuration. From this viewpoint, the receiving surfaces 39 of the wedge members are clearly shown. The receiving surfaces 39 resemble complementary tracks or grooves that can receive the mating surfaces 36. When the mating surface 36 of a wedge member is received in the receiving surface 39 of an adjacent wedge member, the two wedge members are securely coupled.

Figure 3A:
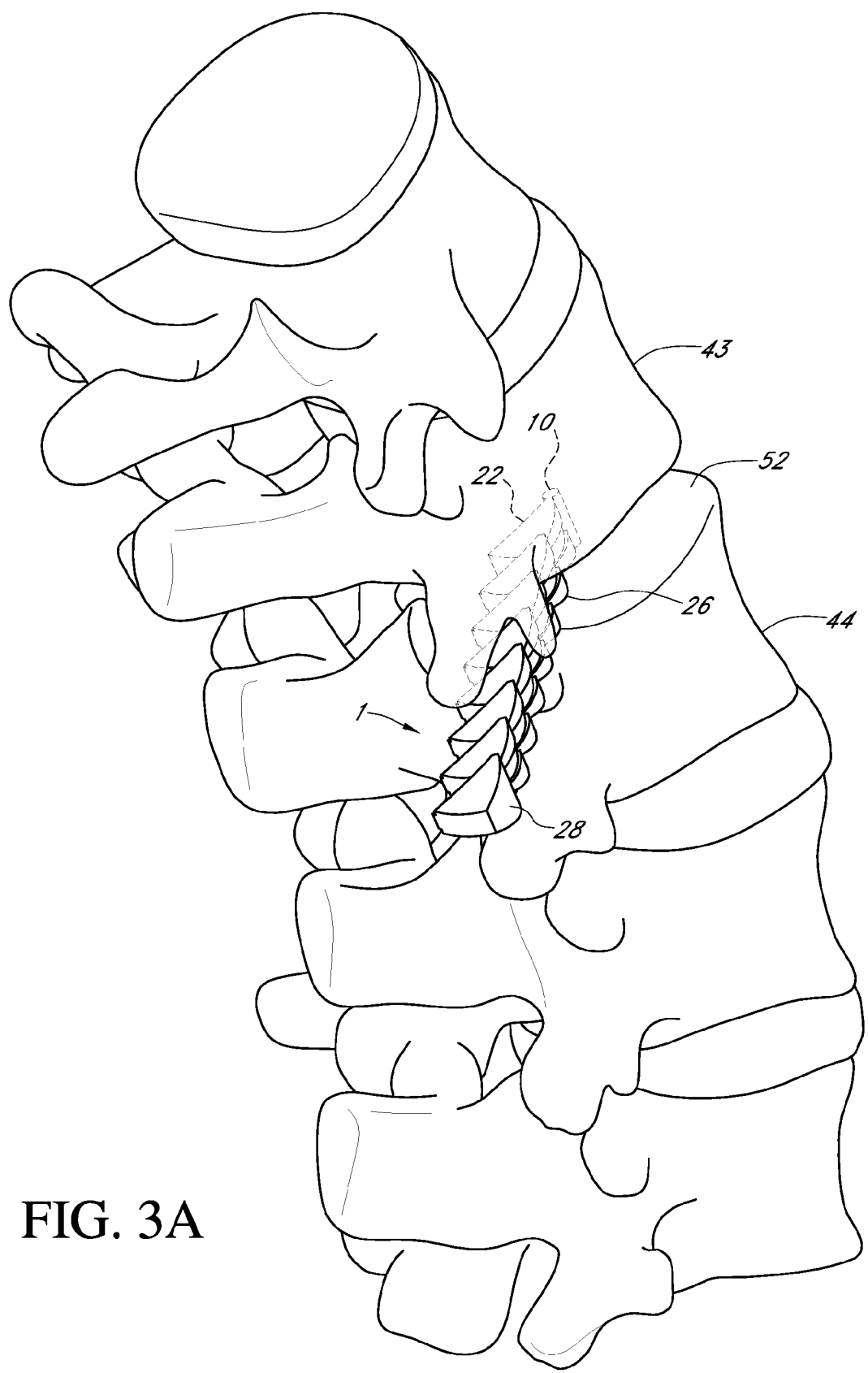
FIGS. 3A-3C illustrate a spinal implant device being implanted in an intervertebral disc space according to one embodiment of the present application.
Figure 3B:
Figure 3C:

FIGS. 3A-3C illustrate a nucleus replacement device in the process of being implanted in an intervertebral disc space according to embodiments of the present application. These figures illustrate a particular sequence of device implantation and illustrate the ease with which the nucleus replacement device 1 can be implanted in a disc space.

FIG. 3A illustrates a nucleus replacement device 1 introduced into a disc space 52 located between a superior vertebra 43 and an inferior vertebra 44. The superior and inferior vertebra can be located anywhere along the spine and can include cervical, thoracic and lumbar vertebrae. As shown in FIG. 3A, prior to introducing the nucleus replacement device 1, the natural nucleus can be completely removed. In other embodiments, only a portion of the natural nucleus need be removed and replaced by the nucleus replacement device 1. In addition, prior to introducing the nucleus replacement device, the volume of the disc space 52 can be measured so that a properly sized nucleus replacement device 1 can be selected prior to insertion.

The nucleus replacement device 1 includes a leading wedge 22 having an anchor 10 at its tip, intermediary wedges 26 and a trailing wedge 28 held internally by a rod member (not shown). The nucleus replacement device 1 is in a first configuration in which the wedge members are placed in a linearly, expanded form that allows the device to be easily inserted into the disc space 52 one at a time and in series. Each of the wedge members is sized such that they can enter a small hole or opening (e.g., such as a flap or incision through an annulus fibrosus). In some embodiments, the wedge members can be introduced in a hole having a size and shape determined, for example, by a surgeon or necessitated by the dimensions of a particular patient and suitable for delivery of the implant.

The leading wedge 22 is introduced first into the disc space 52. After introducing the leading wedge 22 into the disc space 52, the anchor 10 at the tip of the leading wedge 22 can be anchored and positioned relative to one or more vertebrae, such as a superior vertebrae, an inferior vertebrae or both. In some embodiments, the anchor 10 is anchored to a superior vertebra 43 or inferior vertebra 44, while in other embodiments, it is anchored to both the superior vertebra 43 and the inferior vertebra 44. Bone cement can be used in conjunction with the anchor 10 to ensure a tight fit and substantially immobile attachment of the nucleus replacement device 1 to one or more vertebrae.

After anchoring the leading wedge 22 relative to one or more vertebrae, a push rod can be used to push the wedge members off of the rod member (not shown) one at a time. Other suitable components or methods of advancing the wedge members for deliver can also be used. The wedge members that are delivered from the rod member begin to slidably engage with adjacent wedge members and position themselves circumferentially relative to the anchor 10.

FIG. 3B illustrates the nucleus replacement device 1 of FIG. 3A in the process of being placed in the disc space 52. The nucleus replacement device 1 is in an intermediary configuration in which several wedges (including leading wedge 22) have been slidably delivered from the rod member and are positioned circumferentially relative to the anchor 10 in the disc space 52, while other wedge members remain in a linear form outside of the disc space 52. The removed wedge members begin to resemble a portion of the nucleus replacement device in its final circular form.

FIG. 3C illustrates the nucleus replacement device 1 of FIG. 3A positioned in the disc space 52 in its final configuration. Each of the wedge members, including the trailing wedge 28, has been delivered from the rod member and placed circumferentially relative to the anchor 10, which serves as a center axis for the nucleus replacement device 1. In its final configuration, the leading wedge 22 is adjacent the trailing wedge 28. Preferably, the nucleus replacement device 1 fits snugly between the superior vertebra 43 and inferior vertebra 44, and is of a suitable height that separates the adjacent vertebrae. In some embodiments, the nucleus replacement device 1 occupies between about 30% and about 80% of the volume of the disc space 52.

In some embodiments, after being placed in a final configuration in a disc space, the nucleus replacement device can be optionally locked in the final configuration. For example, in some embodiments, the mating surface 36 of the leading wedge 22 and the receiving surface 39 of the trailing wedge 28 can be shaped such that when the two surfaces are mated, the wedge members are locked in place. Other locking mechanisms, including hook members, clasps or adhesives can also be provided.

In some embodiments, after being placed in a final configuration in a disc space, the nucleus replacement device can be removed. In some embodiments, the nucleus replacement device can be removed in its final configuration by providing a large enough opening (e.g., through an annulus fibrosus) that will allow the nucleus replacement device to be removed. In other embodiments, the nucleus replacement includes one or more protrusions or hooks on the surface of a wedge member that allows the wedge member to be pulled out of the final, circular configuration. Applying further pulling force will result in subsequent wedge members being removed and ultimately, re-configured in the initial, linear configuration. In some embodiments, the nucleus replacement device can be delivered and/or removed from a disc space one wedge member at a time, such that the nucleus replacement device is not only easily installed through a small opening, but also easily removed.

In some embodiments, in addition to providing a nucleus replacement device 1 in the disc space 52, an annulus fibrosus replacement (e.g., a matrix of biocompatible fibers) can also be provided that surrounds the nucleus replacement device 1. In other embodiments, the nucleus fibrosus can be left on its own without an annulus fibrosus. In some embodiments, the nucleus replacement device 1 can be inserted into a natural annulus fibrosus, such as through a flap, incision or small opening sized for insertion of the device.

It will be apparent to those skilled in the art that various modifications and variations can be made in the present embodiments without departing from the scope or spirit of the advantages of the present application. Thus, it is intended that the present application cover the modifications and variations of these embodiments and their equivalents.

What is claimed is:

1. A spinal implant system for insertion in a disc space between a superior vertebra and an inferior vertebra comprising:
   a plurality of wedge members comprising a leading wedge, a trailing wedge, and one or more intermediary wedges positioned therebetween, wherein the wedge members are coupled in series and are configured to be delivered to the disc space, wherein each of the plurality of wedge members has a generally triangular cross-section along a longitudinal axis, and wherein each of the plurality of wedge members includes a mating surface on a first side of the wedge member and a receiving surface on a second side of the wedge member for slidably coupling a mating surface of another wedge member, wherein the mating surface of each of the plurality of wedge members comprises a tongue extending along an entire length of the first side and the receiving surface of each of the plurality of wedge members comprises a groove extending along an entire length of the second side; and
   wherein the spinal implant system has a first configuration in which the plurality of wedge members are arranged for delivery to the disc space and a second configuration in which the plurality of wedge members are positioned circumferentially relative to a center axis, and wherein in the second configuration the mating surface of the leading wedge is proximate to the receiving surface of the trailing wedge.

2. A spinal implant system for insertion in a disc space between a superior vertebra and an inferior vertebra comprising:
   a plurality of wedge members comprising a leading wedge, a trailing wedge, and one or more intermediary wedges positioned therebetween, wherein the wedge members are coupled in series and are configured to be delivered to the disc space, wherein the spinal implant system has a first configuration in which the plurality of wedge members are arranged in a linearly expanded form for delivery to the disc space and a second configuration in which the plurality of wedge members are positioned circumferentially relative to a center axis, wherein each of the plurality of wedge members includes a mating surface and a receiving surface for slidably coupling a mating surface of another wedge member, the mating surface comprising a tongue extending along an entire length of a first side of the wedge member and the receiving surface comprising a groove extending along an entire length of a second side of the wedge member, and wherein during delivery to the disc space, the tongue of a first wedge member is slidably received in the groove of an adjacent second wedge member.

3. The spinal implant system of claim 2, wherein one or more of the wedge members is formed of a polymeric material.

4. The spinal implant system of claim 2, further comprising a rod member for holding the plurality of wedge members in the substantially linear configuration.

5. The spinal implant system of claim 2, further comprising a sleeve member for guiding the plurality of wedge members to the disc space.

6. A method of providing a nucleus replacement for an intervertebral disc space in between a superior vertebra and an inferior vertebra of a patient, comprising:
   introducing a nucleus replacement device comprising a plurality of wedge members, including a leading wedge, a trailing wedge and intermediate wedges;
   configuring the nucleus replacement device to be in a first configuration in which the plurality of wedge members are placed in a linear expanded form;
   delivering the nucleus replacement device in the first configuration through a hole in the patient;
   introducing the nucleus replacement device into the intervertebral disc space, wherein the leading wedge is introduced first into the intervertebral disc space; and
   configuring the nucleus replacement device to be in a second configuration in which the plurality of wedge members are placed circumferentially to a central axis within the intervertebral disc space, wherein configuring the nucleus replacement device to be in the second configuration comprises slidably coupling each of the wedge members to an adjacent wedge member such that a tongue extending along an entire length of a first side of a first wedge member is received in a groove extending along an entire length of a second side of an adjacent second wedge member.

7. The method of claim 6, further comprising anchoring the leading wedge via an anchor into the superior vertebra or inferior vertebra.

8. The method of claim 6, wherein the nucleus replacement device is held in the first configuration by a rod member positioned in the plurality of wedge members.

9. The method of claim 8, further comprising using a push rod to push the plurality of wedge members off of the rod member to configure the nucleus replacement device into the second configuration.

* * * * *